United States Patent [19]

Kleber et al.

[11] 4,333,919

[45] Jun. 8, 1982

[54] GROWTH PROMOTANT CONTROLLED RELEASE FORMULATIONS AND METHOD OF TREATMENT

[75] Inventors: John W. Kleber; Barbara E. Simpson, both of Indianapolis, Ind.

[73] Assignee: Eli Lilly and Company, Indianapolis, Ind.

[21] Appl. No.: 216,404

[22] Filed: Dec. 15, 1980

Related U.S. Application Data

[63] Continuation-in-part of Ser. No. 74,682, Sep. 12, 1979, abandoned.

[51] Int. Cl.³ .......................... A61K 9/22; A61K 9/26
[52] U.S. Cl. ............................... 424/15; 424/19; 424/22
[58] Field of Search ........................... 424/19, 22, 15

[56] References Cited

U.S. PATENT DOCUMENTS

| | | | |
|---|---|---|---|
| 3,056,724 | 10/1962 | Marston | 424/22 |
| 3,507,952 | 4/1970 | Rodnick et al. | 424/229 |
| 3,535,419 | 10/1970 | Siegrist | 424/22 |
| 3,736,646 | 6/1973 | Schmitt et al. | 29/458 |
| 3,773,919 | 11/1973 | Boswell et al. | 424/22 |
| 3,844,285 | 10/1974 | Laby | 128/260 |
| 3,887,699 | 6/1975 | Yollos | 424/19 |
| 3,972,999 | 8/1976 | Tsuk | 424/78 |
| 3,976,071 | 8/1976 | Sadek | 128/260 |
| 3,991,766 | 11/1976 | Schmitt et al. | 128/335.5 |
| 4,011,312 | 3/1977 | Router | 424/78 |
| 4,076,798 | 2/1978 | Casey et al. | 424/22 |
| 4,118,470 | 10/1978 | Casey et al. | 424/19 |
| 4,166,107 | 8/1979 | Miller et al. | 424/19 |
| 4,166,800 | 9/1979 | Fong | 252/316 |
| 4,273,920 | 6/1981 | Nevin | 528/361 |

*Primary Examiner*—Shep K. Rose
*Attorney, Agent, or Firm*—Charles W. Ashbrook; Arthur R. Whale

[57] ABSTRACT

Controlled release formulations comprised of a growth promoting agent admixed with a copolymer derived from lactic acid and glycolic acid and which is substantially free of polymerization catalyst are effective in the prolonged growth promotion of ruminants. A method for continuous dosing of active ingredients to a ruminant is provided.

24 Claims, No Drawings

GROWTH PROMOTANT CONTROLLED RELEASE FORMULATIONS AND METHOD OF TREATMENT

CROSS-REFERENCE TO RELATED APPLICATIONS

This is a continuation-in-part of copending application Ser. No. 74,682, filed Sept. 12, 1979 now abandoned.

BACKGROUND OF THE INVENTION

A number of agents are currently known which exhibit a beneficial effect upon feed consumption and utilization in animals when administered in conjunction with normal feed regiments. Some of the most important agents are those which increase the output by domestic animals of products utilized by humans. For example, ruminant animals, such as cattle, sheep and goats, experience an increase in the efficiency of their feed utilization as well as body growth promotion, and wool growth promotion in sheep, when administered effective amounts of growth promotors such as monensin, salinomycin, lasalocid and related compounds. Many of the growth promotors operate by altering the breakdown of food in the rumen of the animal. To be effective, such agents must be deposited in the rumen or reticulo-rumen of the animal.

A major problem associated with drug administration to animals in general is the frequency required and the resulting rise in labor costs necessitated thereby. Moreover, many animals utilized for human food consumption, particularly ruminants such as cattle and sheep, are range fed for extended periods of time prior to feed lot development, thus rendering drug administration by daily dosing or by feed additives virtually impossible, and economically impracticable.

The administration of drugs to animals and humans by prolonged release formulations is known to be effective in some instances. For example, it is known to deposit a drug in an impregnable strip to be worn as a collar around the neck of an animal. The drug slowly released for the prolonged treatment of external parasites. Reuter et al., in U.S. Pat. No. 4,011,312, discloses a prolonged release drug dosage form useful for the treatment of bovine mastitis. Such formulation is comprised of a suitable antimicrobial agent dispersed in a copolymer made up of about 60 to 80 mole percent glycolic acid and 20 to 40 mole percent lactic acid. Such copolymer is said to have a molecular weight of less than 2000. While the copolymer is effective in slowly releasing a therapeutic agent when in contact with the fluids of the teat canal, such copolymer is ineffective for beneficial controlled release when subjected to the fluids of the rumen.

An object of the present invention is to provide formulations designed for controllably releasing an effective amount of growth promotant to a ruminant over a prolonged period of time. A further object of the invention is to provide a method for increasing feed utilization in ruminants. Such method is particularly important in the treatment of range fed animals, since a single treatment according to this invention is effective for several months.

SUMMARY OF THE INVENTION

The invention concerns a controlled release formulation capable of uniformly delivering an efficacious dose of a growth promoting agent to a ruminant animal over a prolonged period of time following a single administration. The invention provides a formulation matrix that is biodegradable into substances naturally occurring in biological systems, with no undesirable residues remaining in animal tissues. More particularly, the invention concerns a controlled release formulation comprising an effective amount of a growth promoting agent uniformly admixed with a copolymeric matrix derived from about 60 to about 95 percent by weight of lactic acid and about 40 to about 5 percent glycolic acid. Said copolymer has an inherent viscosity of about 0.08 to about 0.30 when measured in chloroform, and a molecular weight of about 6000 to about 35000. The copolymer employed in the formulation of this invention is substantially free of polymerization catalyst, thereby obviating the problem of toxic residues following degradation of the copolymer.

A preferred copolymeric matrix utilized in the formulations of the invention is one derived from about 60 to about 90 percent lactic acid and about 40 to about 10 percent glycolic acid, and has an inherent viscosity of about 0.10 to about 0.25. A more preferred formulation is one wherein the copolymer contains from about 70 to about 80 percent lactic units and about 30 to about 20 percent glycolic units, with an inherent viscosity of about 0.13 to about 0.23 and a molecular weight of about 15000 to about 30000.

This invention provides controlled release formulations useful for promoting the growth of ruminant animals and for enhancing the efficiency of utilization of feed by ruminants. The formulations contain as active ingredient from about 20 to about 80 percent by weight of any of the well known and commonly utilized ruminant growth promoting agents. Preferred growth promotors include antibiotics such as monensin, narasin, lasalocid, salinomycin, apramycin, actaplanin, deshydroxymethyl monensin, nigericin, deshydroxymethyl nigericin, dianemycin, erythromycin, vancomycin, ristocetin, soimycin, thiostrepton, desoxynarasin, and related growth promotors.

A particularly preferred formulation provided by this invention comprises a biodegradable dosage form useful for effecting growth promotion in ruminants comprising from about 20 to about 80 percent by weight, most preferably about 30 to about 70 percent, of monensin intimately dispersed throughout a copolymeric matrix derived from about 60 to about 90 percent by weight of lactic acid and about 40 to about 10 percent by weight of glycolic acid, said copolymer having an inherent viscosity of about 0.10 to about 0.25.

This invention additionally provides a method for continuously effecting growth promotion and increasing feed utilization in ruminants comprising administering to a ruminant an effective amount of a controlled release formulation made up of about 20 to about 80 percent by weight of a growth promoting agent admixed with about 80 to about 20 percent by weight of a copolymer derived from about 60 to about 95 weight percent of lactic acid and about 40 to about 5 weight percent glycolic acid, said copolymer being substantially free of polymerization catalyst. According to the method of this invention, ruminants can receive a continuous effective dose of growth promotant over a prolonged period of time following a single administration. Such animals are not subjected to toxic copolymerization catalysts.

A preferred method according to the invention comprises orally administering to a ruminant an effective amount of a formulation comprised of about 30 to about 70 percent by weight of monensin sodium salt admixed with about 70 to about 30 percent of weight of a copolymer derived from about 60 to about 90 weight percent of lactic acid and about 40 to about 10 percent glycolic acid, with an inherent viscosity of about 0.10 to about 0.25.

DETAILED DESCRIPTION OF THE INVENTION

The present invention provides a controlled release formulation which can be placed in the reticulo-rumen of a ruminant and which will uniformly deliver an efficacious dose of growth promoting agent to the animal via the rumen for a period of about 80 to about 160 days. The formulations of this invention utilize a copolymeric material ideally suited to the controlled release of an effective amount of a pharmaceutical agent to an animal such that the animal can be effectively treated with a minimum of administrations. Such copolymer and its preparation is the subject of the copending application of Robert S. Nevin, Ser. No. 75,296 filed Sept. 12, 1979. Such copolymeric material is prepared by a process which permits the substantially complete (ie. greater than about ninety-five percent) removal of polymerization catalyst, thereby permitting the total degradation of the copolymeric matrix in a biological system without the concomitant accumulation of toxic residues in animal tissues. This aspect of the invention is of particular significance in the treatment of animals utilized in the production of meat and other animal products intended for human consumption.

The copolymers required for the formulations of this invention are prepared by condensation of lactic acid and glycolic acid in the presence of a readily removable polymerization catalyst. Such catalysts include strong acid ion-exchange resins in the form of beads or similarly hard structures which are easily removed by filtration or similar techniques. Particularly preferred polymerization catalysts include commercially available strong acid ion-exchange resins such as Amberlite IR-118(H), Dowex HCR-W (formerly Dowex 50W), Duolite C-20, Amberlyst 15, Dowex MSC-1, Duolite C-25D, Duolite ES-26 and related strong acid ion-exchange resins. The catalyst is added to a mixture of about 60 to about 95 parts by weight of lactic acid and about 40 to about 5 parts by weight of glycolic acid. The amount of catalyst utilized is not critical to the polymerization, but typically is from about 0.01 to about 20.0 parts by weight relative to the total weight of combined lactic acid and glycolic acid. The polymerization generally is carried out in the absence of solvents; however, organic solvents such as dimethylsulfoxide or N,N-dimethylformamide can be utilized if desired. The polymerization reaction routinely is carried out in a reaction system equipped with a condensing system, thereby permitting the collection and removal of water that is formed, as well as facilitating the removal of any lactide and glycolide by-products that are formed. The polymerization reaction generally is conducted at an elevated temperature of about 100° to about 250° C., and at such temperature is usually substantially complete within about 48 to about 96 hours. Ideally, the reaction can be carried out under a reduced pressure, thereby further facilitating removal of water and by-products.

The copolymer thus formed is readily recovered by simply filtering the molten reaction mixture, for example through a wire screen, to remove substantially all (ie. about ninety-five percent or more) of the strong acid ion-exchange polymerization catalyst. Alternatively, the reaction mixture can be cooled to room temperature and then dissolved in a suitable organic solvent such as dichloromethane or acetone and then filtered by normal means so as to remove the solvent-insoluble strong acid ion-exchange resin. The copolymer then is isolated by removal of the solvent from the filtrate, for instance by evaporation under reduced pressure. Further purification of the copolymer can be accomplished if desired by re-dissolving it in a suitable organic solvent and further filtration, including the use of standard filter aids if desired.

The copolymer thus formed is required in the formulations and method of treatment provided by this invention. Such copolymers, while not amenable to exact structure elucidation, are characterized as having a molecular weight of about 6000 to about 35000, and ideally about 25000. The copolymers are unique in that they are classified as high molecular weight substances having an inherent viscosity from about 0.08 to about 0.30 when measured by standard techniques utilizing the Ubbelohde viscometer in which chloroform has an efflux time of about 51 seconds at 25° C. The inherent viscosity of the copolymers is determined by the following equations $$\eta r = t/t_o$$

$$\eta inh = \ln \eta r / C$$

wherein:
$\eta r$ is relative viscosity;
$t_o$ is efflux time of solvent;
t is efflux time of the solution;
$\eta inh$ is inherent viscosity;
C is concentration in grams per 100 ml. of solvent; and
ln is logarithum.

The copolymers utilized in the formulations of this invention are additionally unique in that they are capable of providing a controlled release of pharmaceutical agents heretofore unavailable in ruminant fluids.

The formulations comprehended by this invention comprise an effective amount of a pharmacologically active growth promoting agent uniformly admixed and dispersed throughout the copolymeric matrix hereinabove described. The formulations contain about 20 to about 80 percent by weight of active ingredient, ideally 30 to 70 percent. The pharmacologically active agents which can be utilized in the formulations include those agents commonly employed in the promotion of growth and stimulation of feed utilization by ruminants. Commonly used active agents include monensin, narasin, lasalocid, salinomycin, apramycin, actaplanin, deshydroxymethyl monensin, nigericin, deshydroxymethyl nigericin, dianemycin, erythromycin, vancomycin, ristocetin, soimycin, thiostrepton, desoxynarasin and the like. It will be recognized that salts and esters of such compounds can also be used. A particularly preferred formulation according to this invention comprises as active growth promotant the antibiotic monensin (see U.S. Pat. No. 3,839,557) in the form of a sodium salt. Such growth promotant is preferably admixed with a copolymer containing about 70 to about 80 percent lactic units and about 30 to about 20 percent glycolic units, said copolymer having an inherent viscosity of about 0.13 to about 0.23. The formulations of the invention can, if desired, contain more than one active ingredient, as well as any of a number of commonly utilized pharmaceutical diluents, excipients and carriers.

The formulations provided by this invention can be prepared in any of a number of ways including dry mixing, spray drying and the like. A preferred method of preparation comprises dissolving a suitable amount of the aforementioned copolymer in a solubilizing organic solvent that is readily removed by evaporation, and then adding the desired amount of pharamcologically active agent, followed by removal of the organic solvent. For example, about 50 grams of a copolymer derived from about 80 weight percent of lactic acid and about 20 weight percent of glycolic acid, having an inherent viscosity of about 0.18, can be dissolved in about 200 to about 400 ml. of a suitable organic solvent such as dichloromethane, acetone, dimethyl ether, tetrahydrofuran, chloroform, or the like. A pharamcologically active growth promoting agent, such as monensin sodium, lasalocid or salinomycin, in the amount of about 50 g., is then added to the dissolved copolymer. The solution thus formed is stirred for uniform mixing and then the solvent is removed by evaporation, thus providing a uniformly mixed formulation of copolymer and active agent in a solid mass. The solid so formed can be placed in a suitable capsule for convenient oral administration to a ruminant. For instance, the formulation can be administered orally to a range fed calf for effective growth promotion and/or enhanced feed utilization over a prolonged period of time. Such treatment provides uniformly controlled release of growth promotant to the ruminant, such that the effective dose of active ingredient is safe for the animal. Said effective dose typically amounts to less than about 500 mg. per animal each day. Typical daily doses will be about 100 to about 300 mg. per animal. The novel formulation affords treatment to the animal for as long as about 160 days.

The formulations of the invention can alternatively be prepared by first mixing the suitable copolymer and active agent in the powdered dry state in order to provide a uniform powdered mixture. The mixture is next heated to about 80° to about 100° C. for about six to about ten hours to provide a uniformly mixed granulated formulation. The formulation so formed is next extruded, for instance through a standard Killion Extruder, thereby providing a softened uniform mass which can be filled directly into a capsule.

The formulations provided by this invention can contain, in addition to the copolymer matrix and the active ingredient, other substances commonly utilized in medicinal formulations. Diluents, carriers, binders, excipients and adjuvants routinely incorporated in such formulations include gum tragacanth, acacia, corn starch, gelatin, alginic acid, magnesium stearate, aluminum monostearate, span 80, tween 80, sorbitan monostearate, hexaglyceryldistearate, glyceryldistearate, sucrose, lactose, methylparaben, propylparaben, bees wax, mannitol, propylene glycol, microcrystalline cellulose, calcium silicate, silica, polyvinylpyrrolidone, cocoa butter, polyoxyethylene sorbitan monolaurate, ethyl lactate, sorbitan trioleate, calcium stearate, talc and the like.

The formulations contemplated herein can, if desired, include more than one pharmacologically active ingredient. Certain growth promotors, for example, have an immediate onset of action, while others may not be completely effective until normal treatment has been carried out repeatedly. According to this invention, a fast acting growth promotor can be combined with the aforementioned copolymer matrix, together with a slower acting active agent. Administration of such formulation is then effective for increasing feed utilization and promoting growth in the host animal for several months after a single administration. A particularly preferred formulation containing more than one active growth promotor is one containing monensin and lasalocid.

The formulations of this invention are useful when administered to a ruminant and retained in the reticulo-rumen portion of the stomach of such ruminant. In order to function as contemplated, the formulation should be administered in a holder or capsule capable of being retained in the reticulo-rumen of the animal, and having sufficient exposed surface area such that the rumen fluids contact the formulation so that the desired controlled release of active agent is achieved. Any of a number of capsules designed to be retained in the rumen or reticulo-rumen portion of an animal can be utilized for the delivery of a formulation provided by this invention. Typical devices for administration of therapeutic and biologically active substances to ruminants are described in detail by Laby, U.S. Pat. No. 3,844,285. These devices suffer, however, from having less than ideal exposed surface area. A particularly preferred receptacle for use in administering the formulations of this invention is a metal cylinder open at both ends. Such device is described by Simpson in copending application Ser. No. 74,683 filed Sept. 12, 1979. More particularly, a steel cylinder measuring about 20 to about 35 mm. in diameter and about 20 to about 80 mm. in length, weighing from about 60 to about 120 grams when empty, is ideally suited to administration to a ruminant. Such steel capsule is of sufficient weight to remain in the reticulo-rumen of the ruminant. Such steel capsule can be made of mild steel or the like, and preferably coated with a substance such as nickel or a food grade lacquer to diminish depolymerization. Ideally, such steel cylinder is equipped with suitably spaced inner grooves about 30 to about 50 percent of the thickness of the cylinder wall. Such inner grooves will aid retention of the formulation while the device is lodged in the reticulo-rumen of the animal. Pins and similar cross bars can be provided as further retaining means if desired.

For administration to ruminants such as bovine, the steel bolus hereinabove described can be packed with about 35 to about 60 g. of a controlled release formulation of the invention. Such bolus then is ready for oral administration to a calf for the uniform release of the growth promotor and/or feed efficiency enhancer over a period of time of about 80 to about 160 days.

For ruminants such as sheep, a steel capsule about 10 mm. to about 20 mm. in diameter and about 20 to about 30 mm. in length, open at both ends, can be packed with a formulation of this invention for the controlled release of the desired growth promoting agent. Such agents, for instance monensin, cause an increase in feed utilization and/or effect growth in sheep not only of actual weight, but also of their generation of fleece.

The controlled release of active agent from the formulations according to this invention has been demonstrated in both in vitro and in vivo experiments. In a typical in vitro study, a steel capsule measuring 25 mm. by 25 mm. was packed with 11.0 grams of a fifty percent by weight formulation of monensin in a copolymer matrix derived from about 80 percent lactic acid and about 20 percent glycolic acid, said copolymer having an inherent viscosity of about 0.18. The bolus thus prepared (total weight 39.25 g) was placed in a plastic bottle containing 200 ml. of artificial rumen fluid at pH 7.0, prepared according to the method of Cheng et al., *Journal of Dairy Science*, 38, 1225 (1955). The plastic bottle also contained twelve stainless steel ball bearings, each measuring 9 mm. in diameter. The bottle was rotated continuously at 34 rpm at a constant temperature of 39° C. Such conditions simulate the movement and abrasive effects of feed in the rumen of an animal. At twenty-four hour intervals over an eleven day test period, the capsule was removed, dried and weighed. The aqueous solution was removed from the plastic bottle at each twenty-four hour interval and assayed for its monensin content by the colorimetric method of Golab et al., *Journal A.O.A.C.*, 56, 171 (1973). Fresh solution was placed in the bottle at each twenty-four hour interval.

The results of such in vitro experiment are given in Tables I and II below. Table I gives the daily weight reduction of the monensin bolus. Table II gives the quantity of monensin found each day in the rumen-like fluid.

fistula, at 7 to 13 day intervals over about a three month test period. Each bolus was weighed to determine the amount of active ingredient which had been administered to each animal, and then each bolus was returned to the reticulo-rumen via the fistula. The payout of active ingredient to each of the three test animals is given in Table III.

TABLE III
Payout of Monensin from formulations placed in the rumen of fistulated cattle

|  | Animal #1 | Animal #2 | Animal #3 |
|---|---|---|---|
| Gross bolus weight | 142.8 g | 142.3 g | 143.3 g |
| Empty bolus weight | 98.8 g | 97.9 g | 99.0 g |
| Net formulation weight | 44.0 g | 44.4 g | 44.3 g |
| (50% monensin) | | | |
| Payout periods (days) | Estimated Monensin payout mg/head/day (weight loss of the bolus divided by 2) | | |
| 0–7 | 0 | 96 | 100 |
| 7–14 | 164 | — | 221 |
| 14–21 | 243 | 193 | 150 |
| 21–29 | 194 | 200 | 206 |
| 29–42 | 227 | 192 | 246 |
| 42–52 | 175 | 185 | 170 |
| 52–63 | 182 | 195 | 227 |
| 63–72 | — | 183 | 239 |
| 73–79 | — | 71 | 100 |
| 79–86 | — | 121 | 150 |

TABLE I
Monensin in vitro capsule weight change

| days | 0 | 1 | 2 | 3 | 4 | 5 | 6 | 7 | 8 | 9 | 10 | 11 |
|---|---|---|---|---|---|---|---|---|---|---|---|---|
| Weight (grams) | 39.25 | 38.57 | 38.2 | 37.7 | 37.2 | 36.7 | 36.25 | 35.8 | 35.45 | 34.8 | 34.3 | 33.75 |
| Weight change per day (grams) | | −0.5 | −0.55 | −0.5 | −0.5 | −0.5 | −0.45 | −0.45 | −0.35 | −0.65 | −0.5 | −0.55 |
| Cumulative weight change (grams) | | −0.5 | −1.05 | −1.55 | −2.05 | −2.55 | −3.0 | −3.45 | −3.8 | −4.45 | −4.95 | −5.5 |

TABLE II
Daily Monensin content of in vitro rumen fluid

| Day | 1 | 2 | 3 | 4 | 5 | 6 | 7 | 8 | 9 | 10 | 11 |
|---|---|---|---|---|---|---|---|---|---|---|---|
| mg. found | 215 | 228 | 231 | 210 | 208 | 181 | 247 | 151 | 270 | 257 | 178 |
| mg. theory | 250 | 275 | 250 | 250 | 250 | 225 | 225 | 175 | 325 | 250 | 275 |
| Percent of theory found | 86 | 83 | 92 | 84 | 83 | 80 | 110 | 86 | 83 | 103 | 65 |

The in vitro data presented in Tables I and II demonstrate that in a simulated rumen environment, a controlled release formulation of this invention is effective in delivering a controlled and substantially uniform daily dose of active ingredient over an extended period of time.

The controlled release formulations provided by this invention additionally have been evaluated in in vivo systems. In one such study, mature cattle were equipped with a fistula for ready access to the reticulo-rumen portion of the stomach. Preweighed steel boluses, containing a formulation consisting of about 50 percent by weight of monensin sodium salt and 50 percent by weight of a copolymer derived from about 80 percent lactic acid and about 20 percent glycolic acid, were placed, via the fistula, into the rumen of each of three heifers. The animals were permitted to graze as desired, and were allowed to drink water freely. The formulation filled bolus was removed from the animals, via the According to the data presented in Table III, the average daily payout of monensin, from a formulation of this invention containing fifty percent by weight of monensin sodium salt, is about 169 mg/head/day for animal #1, 160 mg/head/day for animal #2 and 181 mg/head/day for animal #3, or a mean average daily dose of about 170 mg/head. Such uniform dosing is continuous for about three months. Once all of the formulation contained in the steel capsule has been released, the empty capsule is of such weight that it simply remains in the reticulo-rumen. Additional filled capsules can be administered as needed, and all such capsules can be removed at the time of slaughter. Such removed capsules can be cleaned and repacked with the same or a different formulation and re-administered to ruminant animals, thereby adding economical benefits to the present invention.

A further embodiment of this invention is a method for promoting the growth of ruminant animals and increasing the efficiency of feed utilization by ruminants over a prolonged period of time. Such method of treatment comprises orally administering to a ruminant a growth promoting amount of a controlled release formulation comprised of a growth promoting agent admixed with a copolymer derived from about 60 to about 95 percent by weight of lactic acid and about 40 to about 5 percent by weight of glycolic acid and having an inherent viscosity of about 0.08 to about 0.30. The method provided herein comprises administering a single dose of a formulation as described hereinabove, which administration is effective for controllably delivering to the reticulo-rumen of a ruminant an efficacious daily dose of the active growth promoting agent over a prolonged period of time from about 80 to about 160 days. Additional single doses of such controlled release formulations can be administered so as to obtain the desired treatment over an indefinite period of time with a minimum number of such administrations.

The method provided by this invention is ideally suited to the growth promotion of ruminants which are not amenable to receiving food additives. Such method renders the growth promotion of range fed ruminants particularly attractive and economical. The method provided by this invention comprehends administering a controlled release formulation containing an effective amount of growth promotor such that the daily dose of active agent to an animal is safe, yet effective to stimulate feed utilization and/or promote growth when the animal partakes of the available food source. The method will be practiced by orally administering an effective amount of controlled release formulation to a ruminant weighing, in the case of sheep, about 40 to about 200 pounds, and for bovine, about 200 to about 2000 pounds. The method is preferably directed to cattle weighing about 200 to about 1600 pounds. Typical range fed calves treated according to this invention will weigh about 350 to about 600 pounds.

The daily dose of active ingredient delivered to a host animal according to this invention will be from about 25 to about 1000 mg., and such daily dose preferably will be from about 25 to about 500 mg. per head. It will of course be recognized that the daily dose provided to a host animal will vary somewhat depending upon the concentration of active ingredient utilized in the controlled release formulation, in addition to the particular growth promoting agent incorporated in the formulation and the specific copolymeric matrix utilized. A preferred method according to the invention comprises administering a controlled release formulation of a growth promotor such as monensin, salinomycin or lasalocid, such that the typical dosage is, for sheep, about 5 to about 20 mg/head/day for an animal weighing about 40 to about 150 pounds, and for calves, about 50 to about 200 mg/head/day, for animals weighing about 400 to about 800 pounds. It is also preferred that such method be carried out utilizing a formulation capable of delivering the desired daily dosage uniformly over a period of time of about 80 to about 120 days. The method according to this invention includes repeated administration so as to obtain the desired treatment for the desired extended period of time.

The method of this invention can be practiced on any ruminant animal, including cattle utilized for beef production, cows utilized for milk production or herd proliferation, sheep which are utilized for meat production or for wool production, and for goats utilized for meat, milk and the like.

In an effort to more fully illustrate particular aspects of this invention, the following detailed examples of the preparation of copolymers and final formulations of the invention are provided. The examples are representative only and should not be construed as limiting in any respect.

EXAMPLE 1

Preparation of Copolymer Matrix

To a 3-neck round bottom flask equipped with a condenser and thermometer were added 355.0 g. of lactic acid, 145.0 g. of glycolic acid and 5.0 g. of Dowex HCR-W2-H ion exchange resin. The mixture was stirred and heated to 130° C. for three hours, during which time 200 ml. of water were distilled and collected. After discarding the water thus produced, stirring and heating were continued and the pressure was gradually reduced by vacuum over three hours, after which time the temperature of the reaction mixture had increased to 150° C. at a final pressure of 5 torr. An additional 5.0 g. of Dowex HCR-W2-H catalyst was added to the reaction mixture, and the mixture then was heated to 170° C. at 5.0 torr for twenty-four hours, and then at 185° C. at 5.0 torr for an additional forty-eight hours. The molten reaction mixture was filtered to remove most of the ion exchange polymerization catalyst, and the filtrate was allowed to cool to room temperature to give 300 g. of a copolymer derived from 65 percent lactic acid and 35 percent glycolic acid. The copolymer was analyzed by proton nuclear magnetic resonance spectrometry and shown to consist of 65 percent lactic units and 35 percent glycolic units.

The viscosity of the copolymer was determined in a Ubbelohde viscometer in which chloroform had an efflux time of 51 seconds at 25° C. The copolymer was dissolved in chloroform at a concentration 0.50 g. per 100 ml. of solvent. Inherent viscosity of the copolymer was then determined according to the formulas:

$$\eta r = t/t_o$$

$$\eta inh = 1 n \eta r / C$$

wherein:
$\eta r$ = relative viscosity
$t_o$ = efflux time of solvent ($CHCL_3$)
$t$ = efflux time of solution
$\eta inh$ = inherent viscosity
$C$ = conc. in grams/100 ml.
$1n$ = logarithm The inherent viscosity of the copolymer was determined to be 0.19 dl/g.

EXAMPLE 2

Following the general procedure set forth in Example 1, 710 g. of lactic acid and 290 g. of glycolic acid were condensed in the presence of a total of 40.0 g. of Amberlyst 15 ion exchange polymerization catalyst to afford 600 g. of copolymer derived from about 70 percent by weight lactic acid and about 30 percent by weight glycolic acid. The copolymer had the following viscosity: 0.18 dl/g.

EXAMPLE 3

Following the general procedure of Example 1, 355.0 g. of lactic acid were condensed with 145.0 g. of glycolic acid in the presence of a total of 10.0 g. of Amberlyst 15 ion exchange polymerization catalyst. After removing the catalyst by filtration, there was provided 300 g. of copolymer derived from about 70 percent by weight of lactic acid and 30 percent by weight of glycolic acid. The copolymer exhibited the following viscosity: 0.18 dl/g.

EXAMPLE 4

Following the general procedure of Example 1, 1080 g. of lactic acid were condensed with 252 g. of glycolic acid in the presence of a total of 25.0 g. of Dowex HCR-W2-H ion exchange polymerization catalyst to give, after removal of the catalyst, 750 g. of a copolymer which was shown by NMR to consist of about 79 percent of lactic units and about 21 percent of glycolic units. The copolymer exhibited the following viscosity: 0.20 dl/g.

EXAMPLE 5

Following the procedure of Example 1, 432 g. of lactic acid were condensed with 101 g. of glycolic acid in the presence of a total of 5.0 g. of Dowex HCR-W2-H ion exchange polymerization catalyst to provide, after work-up, 300 g. of a copolymer derived from about 77 weight percent of lactic acid and about 23 weight percent of glycolic acid. The copolymer had a viscosity of 0.21 dl/g.

EXAMPLE 6

Following the procedure of Example 1, 432 g. of lactic acid were condensed with 101 g. of glycolic acid in the presence of a total of 2.5 g. of Dowex HCR-W2-H ion exchange polymerization catalyst to provide 300 g. of copolymer derived from about 76 weight percent lactic acid and about 24 weight percent glycolic acid. The copolymer had the following viscosities:
0.12 after 24 hours at 170° C.
0.20 after 24 additional hours at 185° C.
0.23 after 40 additional hours at 185° C.

EXAMPLE 7

The procedure of Example 1 was followed to condense 1080 g. of lactic acid with 120 g. of glycolic acid in the presence of a total of 25.0 g. of Dowex HCR-W2-H ion exchange polymerization catalyst. After workup, there was recovered 750 g. of a copolymer derived from about 89 weight percent of lactic acid and about 11 weight percent of glycolic acid having the following viscosity: 0.20 dl/g.

EXAMPLE 8

To a stirred solution of 150 ml. of dichloromethane containing 22.0 g. of a copolymer derived from about 80 percent by weight of lactic acid and about 20 percent by weight of glycolic acid, having an inherent viscosity of about 0.19, was added in one portion 22.0 g. of monensin sodium salt. The solution was stirred at ambient temperature for ten minutes and then the solvent was removed by evaporation under reduced pressure. The solid mass that was obtained was ground and heated to about 100° C. and packed into a steel capsule measuring 35 mm × 50 mm and weighing 98.8 g. Final weight of the packed capsule was 142.8 g.

EXAMPLE 9

To a stirred solution of 40.0 g. of the copolymer prepared as described in Example 7 in 200 ml. of chloroform is added 50.0 g. of salinomycin, 40 g. of beeswax and 500 mg. of sorbitan monostearate. The solution is stirred at 25° C. for several minutes and then the solvent is removed by evaporation under reduced pressure. The residue is dissolved in fresh chloroform and spray dried by conventional means to provide a controlled release formulation of salinomycin ideally suited for oral administration in the form of a molded pill that is weighted with sufficient iron filings.

EXAMPLE 10

A formulation comprised of 5.0 g. of monensin sodium salt in 7.0 g. of a copolymer derived from about 60 weight percent lactic acid and about 40 weight percent glycolic acid, having an inherent viscosity of about 0.20, is extruded into rods and then melted at 100° C. and packed into a steel cylinder measuring 10 mm in diameter and 20 mm in length, said steel cylinder being open at both ends. The bolus thus prepared is orally administered to a sheep weighing 70 pounds for the effective promotion of growth over a four month period.

I claim:

1. A biodegradable controlled release formulation useful in promoting growth and feed utilization in ruminant animals comprising from about 20 to about 80 percent by weight of a growth promoting and feed utilization enhancing agent intimately dispersed throughout a copolymer derived from about 60 to about 95 percent by weight of lactic acid and about 40 to about 5 percent by weight of glycolic acid, said copolymer having an inherent viscosity of about 0.08 to about 0.30 when measured in chloroform, said copolymer having a molecular weight of about 6000 to about 35000 and being substantially free of polymerization catalyst, said formulation being in combination with suitable excipients and carriers therefor.

2. The formulation according to claim 1 wherein the active growth promoting agent is selected from the group consisting of monensin, narasin, lasalocid, salinomycin, apramycin, actaplanin, deshydroxymethyl monensin, nigericin, deshydroxymethyl nigericin, dianemycin, erythromycin, vancomycin, ristocetin, soimycin, thiostrepton and desoxynarasin, and the pharmaceutically acceptable salts and esters thereof where applicable.

3. The formulation of claim 2 wherein the copolymeric matrix is derived from about 60 to about 90 weight percent lactic acid and about 40 to about 10 weight percent glycolic acid and has an inherent viscosity of about 0.10 to about 0.25.

4. The formulation of claim 3 wherein the active growth promoting agent is present in about 30 to about 70 percent by weight.

5. The formulation of claim 4 wherein the copolymeric matrix is derived from about 70 to about 80 percent by weight of lactic acid and about 30 to about 20 percent glycolic acid.

6. The formulation of claim 5 wherein the active ingredient is selected from monensin, monensin sodium, lasalocid, narasin, salinomycin, and nigericin.

7. The formulation of claim 6 wherein the copolymer is derived from about 70 to about 80 percent by weight of lactic acid and about 30 to about 20 percent by weight glycolic acid, and has an inherent viscosity of about 0.13 to about 0.23.

8. The formulation of claim 7 wherein the active ingredient is monensin sodium.

9. The formulation of claim 8 wherein monensin sodium is present in about 50 percent by weight.

10. The formulation of claim 9 wherein the copolymer is derived from about 80 percent by weight lactic acid and about 20 percent by weight glycolic acid.

11. The formulation of claim 1 when compressed into a steel open ended cylinder measuring about 20 to about 40 millimeters in diameter and about 40 to about 80 millimeters in length, containing about 30 to about 60 grams of formulation.

12. The formulation of claim 10 when packed into a steel open ended cylinder measuring about 20 to about 40 millimeters in diameter and about 40 to about 80 millimeters in length and containing about 30 to about 60 grams of formulation.

13. A method for increasing the efficiency of feed utilization by a ruminant animal for a prolonged period of time comprising orally administering to the ruminant an effective amount of the controlled release formulation of claim 1 in such a way that the formulation is retained in the rumen or reticulo-rumen portion of the ruminant stomach.

14. The method of claim 13 wherein the formulation administered is one comprised of an active agent selected from monensin, monensin sodium salt, lasalocid, salinomycin, narasin, and nigericin.

15. The method of claim 14 wherein the formulation administered is one wherein the copolymeric matrix is derived from about 70 to about 80 percent by weight of lactic acid and about 30 to about 20 percent by weight of glycolic acid having an inherent viscosity of about 0.13 to about 0.23.

16. The method of claim 15 wherein the active ingredient is monensin sodium.

17. The method of claim 15 wherein the active ingredient is lasalocid.

18. The method of claim 15 wherein the active ingredient is salinomycin.

19. The method for promoting growth in ruminant animals over a prolonged period of time comprising orally administering to the ruminant an effective amount of the controlled release formulation of claim 1 in such a way that the formulation is retained in the rumen or reticulo-rumen portion of the ruminant stomach.

20. The method of claim 19 wherein the formulation administered is one comprised of an active agent selected from monensin, monensin sodium salt, lasalocid, salinomycin, narasin and nigerisin.

21. The method of claim 20 wherein the formulation administered is one wherein the copolymeric matrix is derived from about 70 to about 80 percent by weight of lactic acid and about 30 to about 20 percent by weight of glycolic acid having an inherent viscosity of about 0.13 to about 0.23.

22. The method of claim 21 wherein the active ingredient is monensin sodium.

23. The method of claim 21 wherein the active ingredient is lasalocid.

24. The method of claim 21 wherein the active ingredient is salinomycin.

* * * * *